United States Patent [19]

Kittl

[11] 3,940,410
[45] Feb. 24, 1976

[54] BIS-BENZONAZOLEDICARBONITRILES
[75] Inventor: Hans Kittl, Riehen, Switzerland
[73] Assignee: Sandoz Ltd., (Sandoz AG), Basel, Switzerland
[22] Filed: Sept. 5, 1974
[21] Appl. No.: 503,277

[30] Foreign Application Priority Data
Sept. 11, 1973 Switzerland.................... 13022/73

[52] U.S. Cl..... 260/307 D; 260/45.8 N; 260/465 D; 260/465 E; 427/158
[51] Int. Cl.²........................................ C07D 263/62
[58] Field of Search............................. 260/307 D

[56] References Cited
UNITED STATES PATENTS
3,798,231   3/1974   Fleck et al.................... 260/307 D
FOREIGN PATENTS OR APPLICATIONS
7,018,750   6/1970   Japan
6,923,025   1969     Japan
6,811,247   1968     Japan Primary Examiner—Raymond V. Rush
Attorney, Agent, or Firm—Gerald D. Sharkin; Richard E. Vila; Joseph J. Borovian

[57] ABSTRACT

Disclosed are compounds of formula I

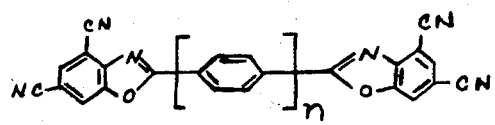

in which $n$ signifies 2 or 3, their production and use as optical brighteners, particularly for polymeric and textile substrates.

3 Claims, No Drawings

BIS-BENZONAZOLEDICARBONITRILES

The invention relates to bis-benzoxazolyl compounds.

The invention provides compounds of formula I,

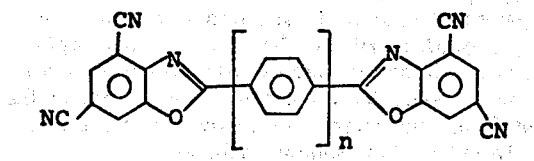

in which $n$ signifies 2 or 3.

The invention also provides a process for the production of compounds of formula I, characterised by a. cyclising a compound of formula II,

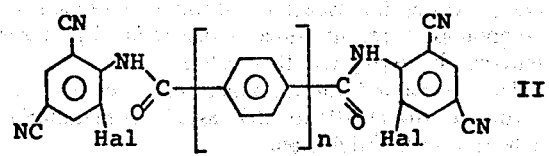

in which $n$ is as defined above, and

Hal signifies chlorine, iodine or, preferably, bromine, or b. reacting a compound of formula III,

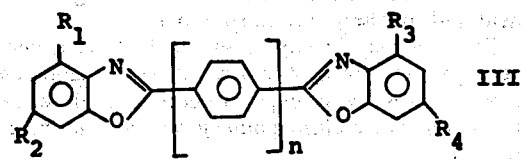

in which $R_1$, $R_2$, $R_3$ and $R_4$, independently, signify chlorine, iodine, bromine or cyano, with the proviso that at least one signifies other than cyano, and $n$ is as defined above, with copper (I) cyanide.

The processes may be carried out in manner conventional for the types of reaction involved.

Thus, the cyclisation reaction in process (a) is conveniently carried in the presence of copper, e.g. powdered copper or finely dispersed copper, or a copper compound. As examples of such copper compounds may be given copper (II) compounds, such as copper (II) oxide, acetate, chloride, bromide and sulphate, and copper (I) compounds, such as copper (I) chloride. Finely dispersed copper may be obtained by reacting lead or zinc with a copper (II) compound, such as copper (II) acetate, chloride or sulphate. The cyclisation is conveniently carried out in an inert organic solvent, such as in hydrocarbons or halogenated or nitrated hydrocarbons, ethers, amides and sulphones. As examples of solvents of the hydrocarbon, halogenated or nitrated hydrocarbon class may be given high-boiling petroleum fractions, xylenes, chlorobenzene, o-di-chlorobenzene, trichlorobenzene, nitrobenzene, bromobenzene, naphthalene, tetrahydronaphthalene and diphenyl. As examples of solvents of the ether class may be given diphenyloxide, methoxy- and ethoxybenzene, bis-(2-ethoxyethyl)-ether, bis-(n-butoxyethyl)-ether, bis-[2-(2'-methoxyethoxy)-ethyl]-ether, bis-[2-(2'-ethoxyethoxy)-ethyl]-ether and bis-[2-(2'-n-butoxyethoxy)-ethyl]-ether. As examples of solvents of the amide class may be given dimethylformamide, dimethylacetamide, and phosphoric acid-tris-(dimethylamide). As example of a solvent of the sulphone class may be given tetramethylene sulphone. The reaction is optionally carried out in the presence of an acid-binding agent. As examples of acid-binding agents may be given the alkali metal salts of weak organic or inorganic acids, e.g. sodium or potassium acetate, or sodium or potassium carbonate, aliphatic amines, e.g. n-butylamine, di-(n-butyl)-amine, tri-(n-butyl)-amine or triethylamine, aliphatic aromatic amines, e.g. dimethylamino- or diethylaminobenzenes, and heterocyclic amines, e.g. pyridine, quinoline, mixtures of pyridine bases, picolines and lutidines. Where desired, the acid binding agent may be employed in excess, the excess serving as solvent. Complex salts may also be used, e.g. derived from reaction of a copper compound and ammonia or pyridine, e.g. cupric ammonium acetate or cupric pyridinium sulphate. A suitable reaction temperature is from 100° to 200°C, preferably from 150° to 200°C where an inorganic acid-binding agent or no acid-binding agent is used, and preferably from 100 to 150°C when an organic acid-binding agent is used.

The cyano exchange reaction of process (b) is suitably carried out in a solvent, e.g. in dimethylformamide, dimethylacetamide, hexamethyl phosphorus triamide, N-methylpyrrolidone, lutidine, picoline, pyridine or, preferably, quinoline. A suitable reaction temperature is from 150° to 250°C, preferably at the reflux temperature of the reaction medium, which medium is advantageously chosen so as to have a reflux temperature of about 200°C. The copper (I) cyanide is advantageously used in excess, e.g. up to 100%, preferably 10 to 50%, above the stoichiometric amount. In the compounds of formula III, preferably all of $R_1$, $R_2$, $R_3$ and $R_4$ signify a halogen, the preferred halogen being bromine. Process (b) is the preferred process.

The resulting compounds of formula I may be isolated and purified in conventional manner.

The compounds of formula II, used in process (a) may be obtained by reacting a compound of formula IV,

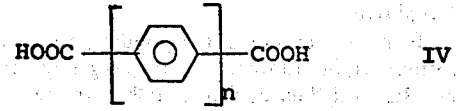

in which $n$ is as defined above, or a functional derivative thereof, with a compound of formula V,

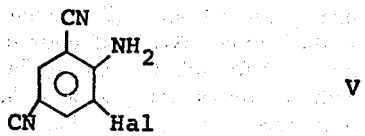

in which Hal is as defined above, preferably bromine.

The reaction may be carried out in conventional manner. Thus, the reaction is conveniently carried out in a high boiling organic solvent, such as in an ether alcohol, e.g. di- or triethylene glycol, di- or tripropylene glycol, 2-(2'-methoxy-ethoxy)-ethanol, 2(2'-ethoxyethoxy)-ethanol or 2-(2'-n-butoxy-ethoxy)-ethanol; in an ether, e.g. diphenyloxide, bis-(2-ethoxyethyl)-ether or bis-(2-n-butoxyethyl)-ether; in an ester, e.g. dibutylphthalate; in a hydrocarbon or halogenated or nitrated hydrocarbon, e.g. polyalkylbenzenes with 2 to 5 methyl and/or ethyl groups, diphenyl, tetrahydronaphthalene, 1,2-dichlorobenzene, trichlorobenzenes or nitrobenzene; in an amide, e.g. phosphoric acid-tris-(dimethylamide), dimethylacetamide; in a sulphone, e.g. tetramethylene sulphone; or in mixtures of such solvents. As examples of functional derivatives of compounds of formula IV may be given the lower alkyl esters, e.g. of 1 to 4 carbon atoms, and the acid halide, i.e. chlorine, bromide and iodide, preferably chloride, derivatives. A suitable reaction temperature is from 0° to 250°C, preferably from 100° to 220°C where an acid chloride derivative of compound IV is employed. Conveniently, the reagents are admixed at a low temperature, e.g. 0°C or, preferably, room temperature, and then the temperature raised, preferably to reflux temperature of the reaction medium.

If desired, the compounds of formula II need not be isolated, the ring closure of process a) being carried out in one and the same medium, the medium being selected to be compatible both with production of compounds of formula II and the ring closure.

The compounds of formula III, above, used in process (b), may be obtained by reacting a compound of formula IV, above, or a functional derivative thereof, with a compound of formula VI,

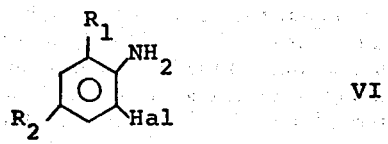

VI and a compound of formula VII

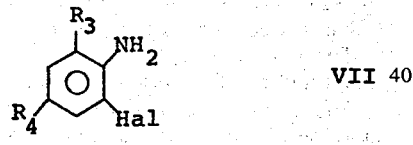

VII in which Hal and $R_1$, $R_2$, $R_3$ and $R_4$ are as defined above,
to form a diamide corresponding to compounds of formula II, but in which the cyano groups are $R_1$, $R_2$, $R_3$ and $R_4$, and then cyclising such diamide.

The reaction of compound IV, or the functional derivative thereof, with compounds VI and VII is conveniently carried out in like manner to the process above described for the production of compounds II. Likewise, the cyclisation of the resulting diamide is conveniently carried out in like manner to process (a), described above. Again, if desired, the resulting compound of formula II need not be isolated but reacted with the copper (II) cyanide in the medium in which it is produced, such medium being selected as to be compatible with the reaction with the copper (I) cyanide.

The compounds of formulae IV, V, VI and VII are either known or may be obtained in conventional manner from available starting materials.

The compounds of formula I are useful as optical brightening agents. They are particularly useful for the brightening of natural, semi-synthetic and fully synthetic textile substrates and also synthetic or semi-synthetic polymeric materials, e.g. polyester (particularly fibre forming polyester), polyamide, polyurethane, polyolefin (e.g. polyethylene and polypropylene), polyvinyl acetate, polyvinyl chloride, polyvinylidene chloride, polyacrylonitrile, modified polyacrylonitrile, cellulose triacetate, cellulose 2½ acetate and polystyrene materials. Such materials may be, for example, in varnish, film, strip, sheet, moulded, fibre or filament form, as appropriate. The compounds of formula I may be incorporated therein in conventional manner, e.g. by being finely distributed or dissolved therein or by being admixed with the monomers or precondensates prior to polymerisation. Where the material is in fibre or filament form, the compounds of formula I are conveniently added to the spinning solution.

For the brightening of textile substrates, whilst the compounds of formula I may be incorporated into the fibres or filaments, they may also be applied to the substrate either in solution form (dissolved in an organic solvent) or in finely distributed form, e.g. from aqueous dispersions. When used on polyester containing substrates, it is especially advantageous to apply the compounds from an aqueous dispersion by padding, followed by drying and thermofixation.

The compounds of formula I may be used in an amount of from 0.001 to 0.5% based on the material or substrate to be brightened.

A particularly preferred use of the compounds of formula I is for the optical brightening of polyesters by incorporation in the melt.

The brightenings obtained by the compounds of formula I possess a particularly notable neutral to violet blue fluorescence and are notably fast to light, chlorite, heat and oxidising bleach solutions.

The following Examples, in which all parts and percentages are by weight, unless otherwise stated, and all temperatures are in degrees centigrade, illustrate the invention. The melting points given have not been corrected.

EXAMPLE 1

15 Parts of bis-(4.6-dibromobenzoxazolyl)-terphenyl are heated to 230° with 8.3 parts of copper-I-cyanide and 300 parts by volume of quinoline in an inert atmosphere with good stirring for 1 hour. The temperature is then kept constant for 2.5 hours, the dark brown solution is cooled to 10°, is filtered and the residue is washed with 150 parts by volume of acetone, then 5 times with 250 parts by volume of aqueous ammonia and finally with 1000 parts of water. After vacuum-drying at 80°, 10 parts are obtained which correspond to 92.6% in theory of a bright yellow product having a melting point of >360°, which may be further purified by recrystallisation from o-dichlorobenzene and corresponds to formula

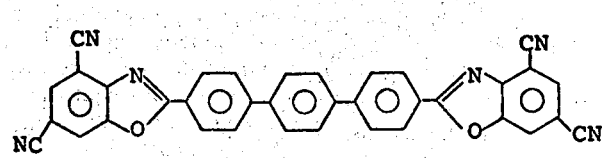

Absorption: λ max: 375 nm in trichlorobenzene, ε = $6.5 \times 10^4$
Emission: λ max: 422 nm in trichlorobenzene
The bis-(4.6-dibromobenzoxazolyl)-terphenyl was obtained as follows:
100 parts of terphenyl dicarboxylic acid are heated to reflux with 1000 parts by volume of thionyl chloride and 5 parts by volume of dimethyl formamide with stirring over the course of 1 hour, and the mixture is kept at this temperature for 4 hours. Subsequently, the excess thionyl chloride is distilled off, cooled to room temperature, 200 parts by volume of benzene are added and it is filtered. After washing with ice water, it is vacuum dried at 80° and 79 parts of the yellow crystalline dicarboxylic acid chloride having a melting point of 219° to 222° are obtained.

35.5 parts of terphenyl dicarboxylic acid chloride are heated to 220° with 66 parts of 2,4,6-tribromoaniline and 1300 parts by volume of dry trichlorobenzene for 60 minutes with stirring and under a nitrogen atmosphere, and the mixture is stirred for 12 hours at this temperature. It is then cooled, filtered and washed with 100 parts by volume of methanol. 85.5 Parts of terphenyl-4,4′-dicarboxylic acid-N,N′-bis-(2,4,6-tribromophenylamide) having a melting point of 360° are obtained. 47.1 Parts of this compound are heated with stirring to 150° with 900 parts by volume of N,N-dimethylacetamide, 390 parts by volume of α-picoline and 22 parts of copper-II-acetate, as well as 3.6 parts of zinc dust. The reaction mixture is kept at this temperature for at least 10 hours, it is cooled to room temperature and the yellowish precipitate is filtered off. 26 Parts of bis-(4,6-dibromobenzoxazolyl)-terphenyl having a melting point of >360° are obtained.

EXAMPLE 2

If the 15 parts of bis-(4,6-dibromobenzoxazolyl)-terphenyl in Example 1 are replaced by 14.1 parts of 4,4′-bis-(4,6-dibromobenzoxazolyl)-biphenyl, and the procedure is as described above, 8.2 parts of a yellowish compound which melts at >360° after recrystallisation from trichlorobenzene and corresponds to formula

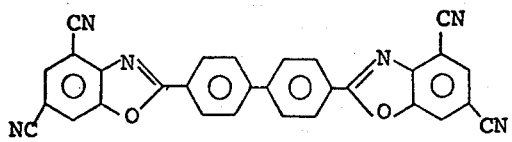

are obtained.
Absorption: λ max: 365 nm in trichlorobenzene
Emission: λ max: 430 nm in trichlorobenzene The necessary initial compounds are synthesised in a similar manner to that of the terphenyl series.

APPLICATION EXAMPLE A 200.0 Parts of polyethylene terephthalate are melted in a container in a nitrogen atmosphere at 280° and 0.04 parts of the compound of Example I are added. The brightening agent is stirred into the polyester until a homogeneous solution is obtained. 4 Parts of titanium dioxide are then added as a dulling agent and the entire matter is stirred again until a homogeneous mixture is obtained. The latter is then pressed through a spinneret and and the filament obtained is first cooled by a spray of water and then stretched and wound onto coils in the normal manner. Products produced from these fibre materials have a considerably better colour than those produced by the same method but withoug the addition of the brightening agent.

Similar whitening effects are obtained if the compound of Example I is used instead of the compound of Example 2.

APPLICATION EXAMPLE B 100.0 parts of polyester granulate are powdered in a mixing apparatus with 0.02 parts of the compound of Example 1, and then subjected to injection moulding. The products obtained have a better appearance than those produced without the addition of the brightener. Similar whitening effects are obtained if the compound of Example 1 is replaced by the compound of Example 2.

What is claimed is:
1. A compound of formula I,

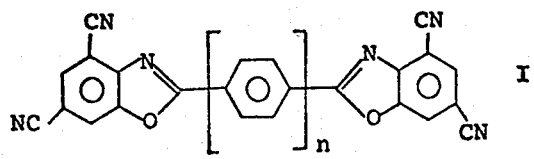

in which $n$ signifies 2 or 3.
2. A compound of claim 1, in which $n$ is 2.
3. A compound of claim 1, in which $n$ is 3.

* * * * *